United States Patent
Anglada et al.

(10) Patent No.: US 8,008,486 B2
(45) Date of Patent: Aug. 30, 2011

(54) PROCESS FOR THE MANUFACTURE OF A CRYSTALLINE PYRAZOLO[1,5-A]PYRIMIDINE COMPOUND

(75) Inventors: Luis Anglada, Barcelona (ES); Albert Palomer, Barcelona (ES); Antonio Guglietta, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 251 days.

(21) Appl. No.: 12/445,221

(22) PCT Filed: Oct. 10, 2007

(86) PCT No.: PCT/EP2007/060796
§ 371 (c)(1),
(2), (4) Date: Jun. 11, 2009

(87) PCT Pub. No.: WO2008/043799
PCT Pub. Date: Apr. 17, 2008

(65) Prior Publication Data
US 2010/0048896 A1    Feb. 25, 2010

Related U.S. Application Data

(60) Provisional application No. 60/851,011, filed on Oct. 11, 2006.

(30) Foreign Application Priority Data
Oct. 11, 2006  (EP) ..................................... 06122143

(51) Int. Cl.
*C07D 487/00*    (2006.01)
(52) U.S. Cl. ......................................................... 544/262
(58) Field of Classification Search ........................ None
See application file for complete search history.

(56) References Cited

U.S. PATENT DOCUMENTS
6,399,621 B1    6/2002    Dusza et al.

FOREIGN PATENT DOCUMENTS
WO    WO-2006/136530 A    12/2006

*Primary Examiner* — Jeffrey Murray
(74) *Attorney, Agent, or Firm* — Birch, Stewart, Kolasch & Birch, LLP

(57) ABSTRACT

The present invention relates to a novel process for the industrial manufacture of polymorph B of N-{2-Fluoro-5-[3-(thiophene-2-carbonyl)-pyrazolo[1,5-a]pyrimidin-7-yl]-phenyl}-N-methyl-acetamide.

8 Claims, 3 Drawing Sheets

PROCESS FOR THE MANUFACTURE OF A CRYSTALLINE PYRAZOLO[1,5-A]PYRIMIDINE COMPOUND

This application is the National Phase of PCT/EP2007/060796 filed on Oct. 10, 2007, which claims priority under 35 U.S.C. 119(e) to U.S. Provisional Application No. 60/851,011 filed on Oct. 11, 2006 and under 35 U.S.C. 119(a) to Patent Application No. EP 06122143.8 filed in Europe on Oct. 11, 2006, all of which are hereby expressly incorporated by reference into the present application.

The present invention relates to a process for the manufacture of polymorph B of N-{2-Fluoro-5-[3-(thiophene-2-carbonyl)-pyrazolo[1,5-a]pyrimidin-7-yl]-phenyl}-N-methyl-acetamide.

BACKGROUND OF THE INVENTION

N-{2-Fluoro-5-[3-(thiophene-2-carbonyl)-pyrazolo[1,5-a]pyrimidin-7-yl]-phenyl}-N-methyl-acetamide is a potent ligand of γ-aminobutyric acid A ($GABA_A$) receptors useful in the treatment or prevention of anxiety, epilepsy, sleep disorders, and insomnia, for inducing sedation-hypnosis, anesthesia, and muscle relaxation, and for modulating the necessary time to induce sleep and its duration, such as described in PCT/EP2006/063243 and U.S. 60/692866.

Throughout the present application the term "compound (I)" refers to N-{2-Fluoro-5-[3-(thiophene-2-carbonyl)-pyrazolo[1,5-a]pyrimidin-7-yl]-phenyl}-N-methyl-acetamide. Crystal form of compound (I) obtained in the above applications is coded here polymorph A.

This form of compound (I) shows a melting point of 165-167° C. In the present research this form showed a DSC with a sharp melting peak between 166.2° C. and 167.4° C. The slight difference with the previously reported melting point is acceptable and is within the range of experimental error. This form is coded here polymorph B.

SUMMARY OF THE INVENTION

The present invention concerns a process for the industrial manufacture of a new form of N-{2-Fluoro-5-[3-(thiophene-2-carbonyl)-pyrazolo[1,5-a]pyrimidin-7-yl]-phenyl}-N-methyl-acetamide, polymorph B, which comprises the synthesis in situ of compound (I) followed by addition of a ($C_1$-$C_4$)-alcohol to the reaction mixture to cause the precipitation of the final product, which is isolated as a solid by filtration.

Polymorph B of compound (I) shows a powder X-Ray diffraction pattern containing the most intense peaks at 2θ=7.1°(±0.1°) and 21.4°(±0.1°). Polymorph B of compound (I) also shows a FT-Raman Spectrum with characteristic signals at 3107 $cm^{-1}$, 1605 $cm^{-1}$, 1593 $cm^{-1}$, 1538 $cm^{-1}$, 1336 $cm^{-1}$, and 102 $cm^{-1}$ and a Differential Scanning Calorimetry with a melting peak at approximately 158° C.

In comparison with polymorph A, polymorph B of compound (I) can be conveniently handled and processed because of its higher stability. This is of importance, not only from the point of view of obtaining a commercially viable manufacturing process, but also from the point of subsequent manufacture of pharmaceutical formulations comprising the active compound. The drug substance, and compositions containing it, are capable of being effectively stored over appreciable periods of time, without exhibiting a significant change in the active component's physicochemical characteristics.

BRIEF DESCRIPTION OF THE DRAWINGS

The invention is described in connection with the appended drawings in which.

DETAILED DESCRIPTION OF THE INVENTION

Figure 1:
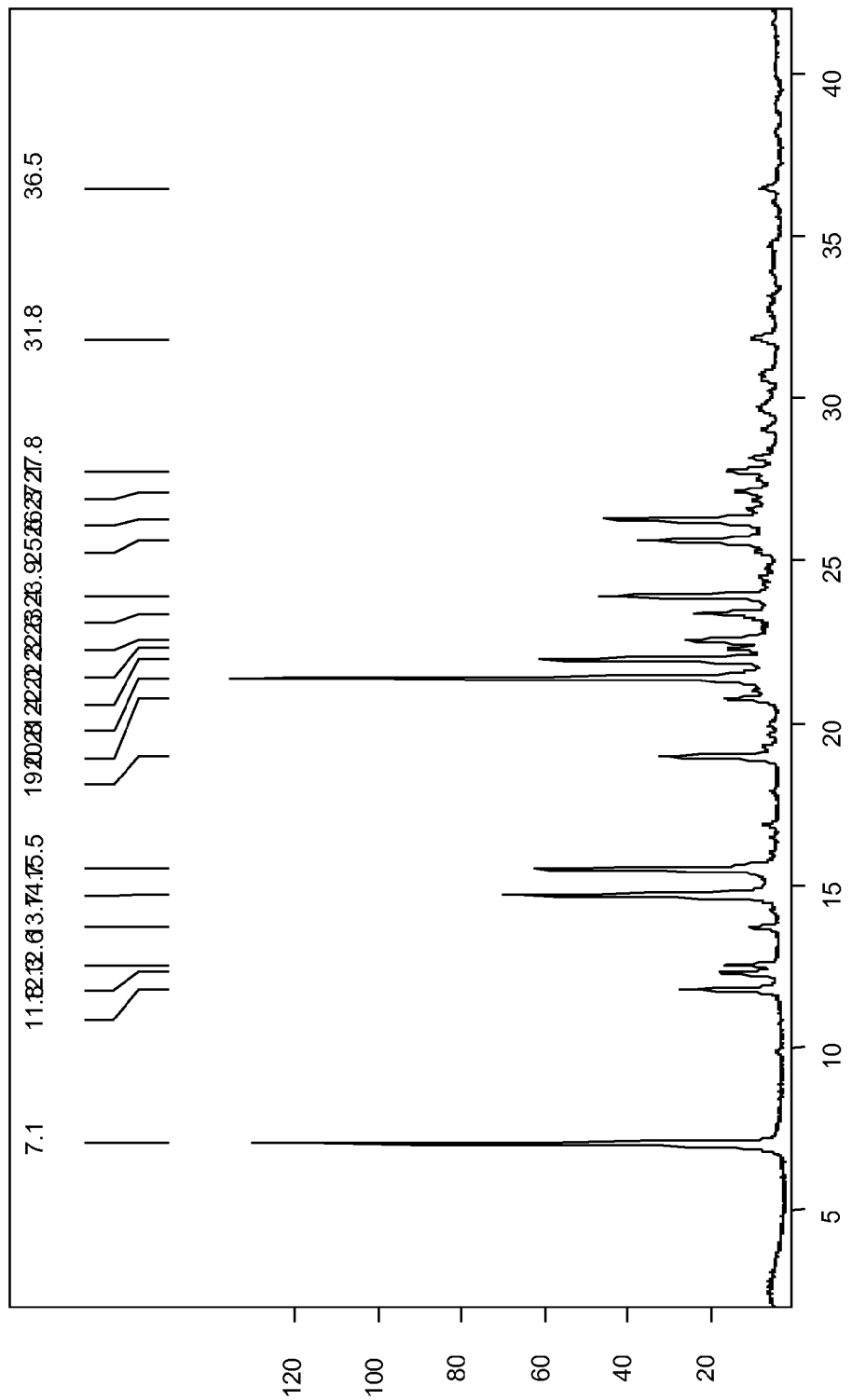
FIG. 1 is the Powder X-Ray Diffraction curve of polymorph B. The Intensity, on the ordinate, is expressed in cps.

The applicants have discovered that the preparation of compound (I) in situ by reaction of (5-amino-1H-pyrazol-4-yl)-thiophen-2-yl-methanone and N-[5-(3-dimethylamino-acryloyl )-2-fluoro-phenyl]-N-methyl-acetamide in acetic acid, followed with addition of a ($C_1$-$C_4$)-alcohol such as 2-propanol, in combination with selected operating conditions, is of great importance in enabling a final substance to be obtained smoothly without problems of reproducibility, quality and yield.

According to the present invention, a more efficient industrial manufacturing process is provided which affords high yield and constant purity standards kilogram-scale preparations of polymorph B of N-{2-Fluoro-5-[3-(thiophene-2-carbonyl)-pyrazolo[1, 5-a]pyrimidin-7-yl]-phenyl}-N-methyl-acetamide which circumvents the above-mentioned problems. Thus, in a first embodiment, the present invention consists in a process for the industrial manufacture of polymorph B of N-{2-Fluoro-5-[3-(thiophene-2-carbonyl)-pyrazolo[1, 5-a]pyrimidin-7-yl]-phenyl}-N-methyl-acetamide which comprises the following steps:

(i) reacting (5-amino-1H-pyrazol-4-yl)-thiophen-2-yl-methanone with N-[5-(3-dimethylamino-acryloyl)-2-fluoro-phenyl]-N-methyl-acetamide in a solvent selected from the group consisting of acetic acid, propionic acid, and formic acid at a temperature ranging from 50° C. to the boiling point of the mixture;

(ii) adding a ($C_1$-$C_4$)-alcohol such as methanol, ethanol, 2-propanol, or 1-propanol; at a temperature comprised between 40° C. and 80° C.;

(iii) aging for at least 30 min. at a temperature comprised between 30 and 55° C. to initiate the crystallization; and (iv) recovering the crystallized product.

Step (I) of the process can also be carried out in an alcohol such as methanol, ethanol, 2-propanol, 1-propanol; dimethylformamide or dimethylsulfoxide.

In a particular embodiment, the process comprises the following steps:

(i) the reaction of (5-amino-1H-pyrazol-4-yl)-thiophen-2-yl-methanone and N-[5-(3-dimethylamino-acryloyl)-2-fluoro-phenyl]-N-methyl-acetamide in acetic acid at a temperature ranging from 100° C. to the boiling point with stirring, under nitrogen medium;

(ii) cooling the reaction mixture to 40-80° C. and adding 2-propanol;

(iii) cooling the reaction mixture to 30-55° C.; and aging for ½ to 2 hours;

(iv) cooling the reaction mixture over 2-3 hours to 0-10° C.; aging for 1 to 4 hours; filtering and washing the resulting crystalline material with 2-propanol; and drying the product under vacuum at 40-60° C.

In another embodiment, the preferred process temperature in step (i) is comprised between 115° C. and 125° C. In another particular embodiment, the preferred temperature is 100° C.

In another embodiment, the reaction mixture in step (ii) is cooled to 60-70° C.

In another embodiment, the reaction mixture in step (iii) is cooled to 40-45° C.

In another embodiment, the aging in step (iii) takes at least 1 hour.

In another embodiment, the crystallized product is recovered by cooling the mixture at a temperature comprised between 0 and 10° C., followed by filtering the obtained product. In a more preferred embodiment, the reaction mixture in step (iv) is cooled for at least 1 hour to 0-5° C.

In another embodiment, the aging in step (iv) takes at least 2 hours, preferably, over 2.5 hours.

In another embodiment, the product in step (iv) is dried at a temperature comprised between 45 and 55° C.

The invention and the best mode of carrying out the same are illustrated by the following non-limitative example.

EXAMPLE 1

Polymorph B of N-{2-Fluoro-5-[3-(thiophene-2-carbonyl)-pyrazolo[1,5-a]pyrimidin-7-yl]-phenyl}-N-methyl-acetamide A 300 L vessel was flushed with nitrogen. Acetic acid (40.0 L) was charged, and then 7.312 kg (37.84 moles) of (5-amino-1H-pyrazol-4-yl)-thiophen-2-yl-methanone and 10.000 kg (37.84 moles) of N-[5-(3-dimethylamino-acryloyl)-2-fluoro-phenyl]-N-methyl-acetamide were added consecutively. The mixture was heated to 120° C. (±5° C.) with stirring. The reaction was controlled by HPLC until completion (<1% of each starting material), which typically occurs in 4 hours. The reaction mass was cooled to 60-70° C. 2-Propanol (80.0 L) was charged to reaction mixture, cooled to 40-45° C. and aged for at least 1 hour. The mixture was cooled over approximately 2.5 hours to 0-5° C. and aged for at least 2 hours. Solids were filtered and washed twice with 10.0 L of chilled 2-propanol. The solid product was dried under vacuum at 50° C. (±5° C.) to remove residual solvents (<0.5% w/w of acetic acid and <0.5% w/w of 2-propanol). N-{2-fluoro-5-[3-(thiophene-2-carbonyl)-pyrazolo[1,5-a]pyrimidin-7-yl]-phenyl}-N-methyl-acetamide was obtained as a crystalline material (12.686 kg). Yield 85%. Purity ≧95%.

$^1$H NMR(400 MHz, CDCl$_3$): δ 1.98 (3H, s,), 3.3 (3H, s), 7.13 (1H, d, J=4 Hz), 7.18-7.20 (1H, m), 7.42 (1H, t, J=8.8 Hz), 7.71 (1H, d, J=5.2 Hz), 8.02-8.08 (2H, m), 8.12 (1H, dd, J=2.4 and 7.6 Hz), 8.71 (1H, s), 8.82 (1H, d, J=4 Hz).

MS (ES) m/z=395 (MH$^+$)

The obtained crystalline material was identified as polymorph B using the following procedures.

Instrumental and Experimental Conditions

Powder X-Ray Diffraction: Bruker D8 Advance. Cu Kα radiation; tube power 35 kV/45 mA; detector VANTEC1; 0.017° 2θ step size, 105±5 s per step, 2°-50° 2θ scanning range (printed range may be different). Silicon single crystal sample holders were used, sample diameter 12 mm, depth 0.1 mm.

FT-Raman Spectroscopy: Bruker RFS100. Nd:YAG 1064 nm excitation, 100 mW laser power, Ge-detector, 64 scans, range 50-3500 cm$^{-1}$, 2 cm$^{-1}$ resolution, Aluminum sample holder.

Differential Scanning Calorimetry: Perkin Elmer DSC 7. Gold crucibles, heating rates of 2 C min$^{-1}$ or 10° C. min$^{-1}$, varying start and end temperatures.

Single-Crystal X-Ray Diffraction: The crystal was measured on a Nonius Kappa CCD diffractometer at 173° K. using graphite-monochromated Mo Kα radiation with λ=0.71073 Å. The COLLECT suite was used for data collection and integration. The structure was solved by direct methods using the program SIR92. Least-squares refinement against F was carried out on all non-hydrogen atoms using the program CRYSTALS. Sheldrick weights were used to complete the refinement. Plots were produced using ORTEP III for Windows.

Results

Powder X-Ray Diffraction: The most intense peaks in the X-ray diffractogram were located at 2θ=7.1°(±0.1°) and 21.4°(±0.1°). The X-Ray diffractogram is shown in FIG. 1.

Figure 2:
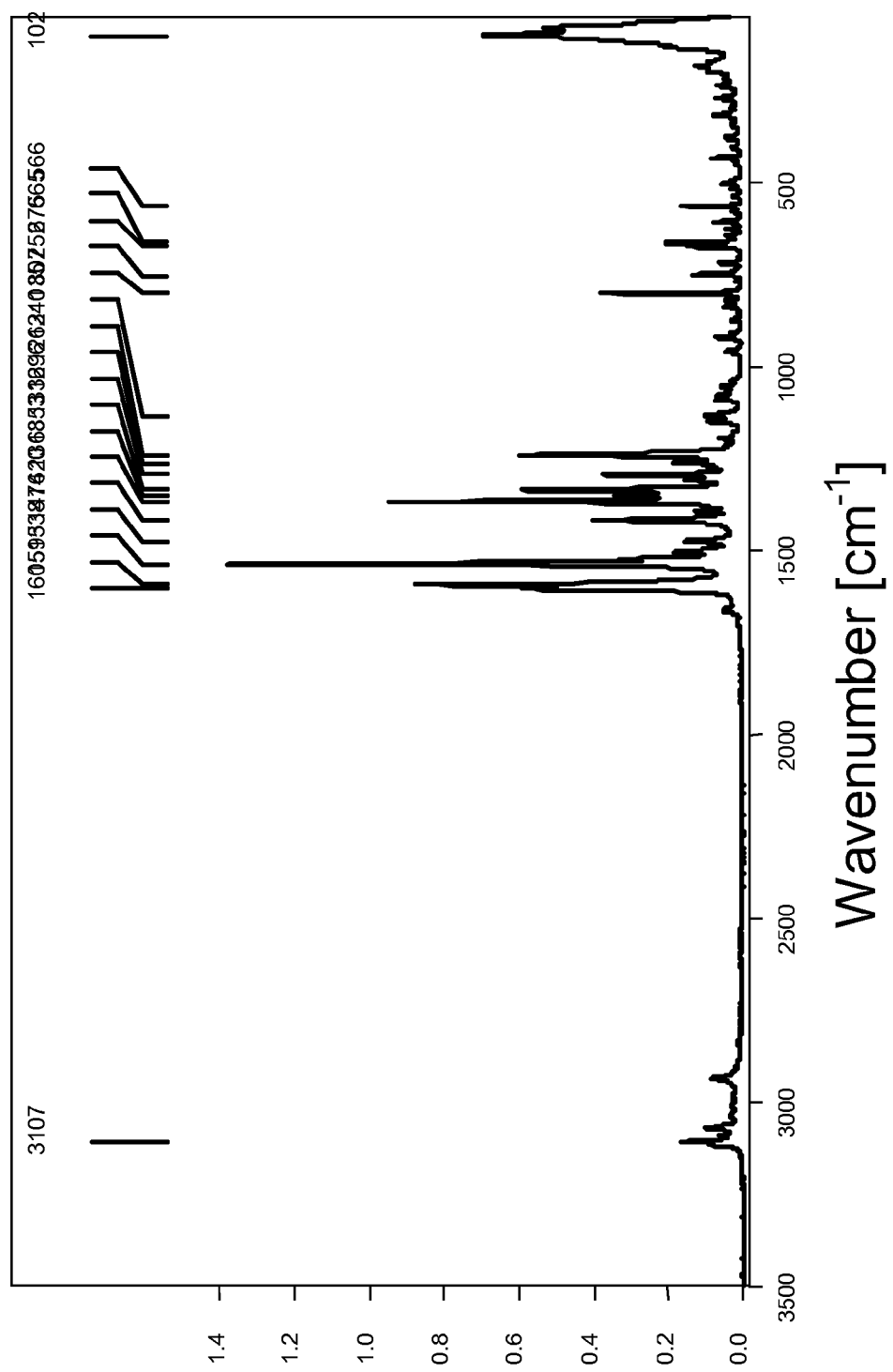
FIG. 2 is the Fourier-Transform Raman (FT-Raman) Spectrum of polymorph B.

FT-Raman Spectroscopy: Characteristic signals in the Raman spectrum of polymorph B were found at 3107 cm$^{-1}$ (most intense peak in the C-H region), 1605 cm$^{-1}$, 1593 cm$^{-1}$, 1538 cm$^{-1}$, 1336 cm$^{-1}$, and 102 cm$^{-1}$. The FT-Raman spectrum is shown in FIG. 2.

Figure 3:
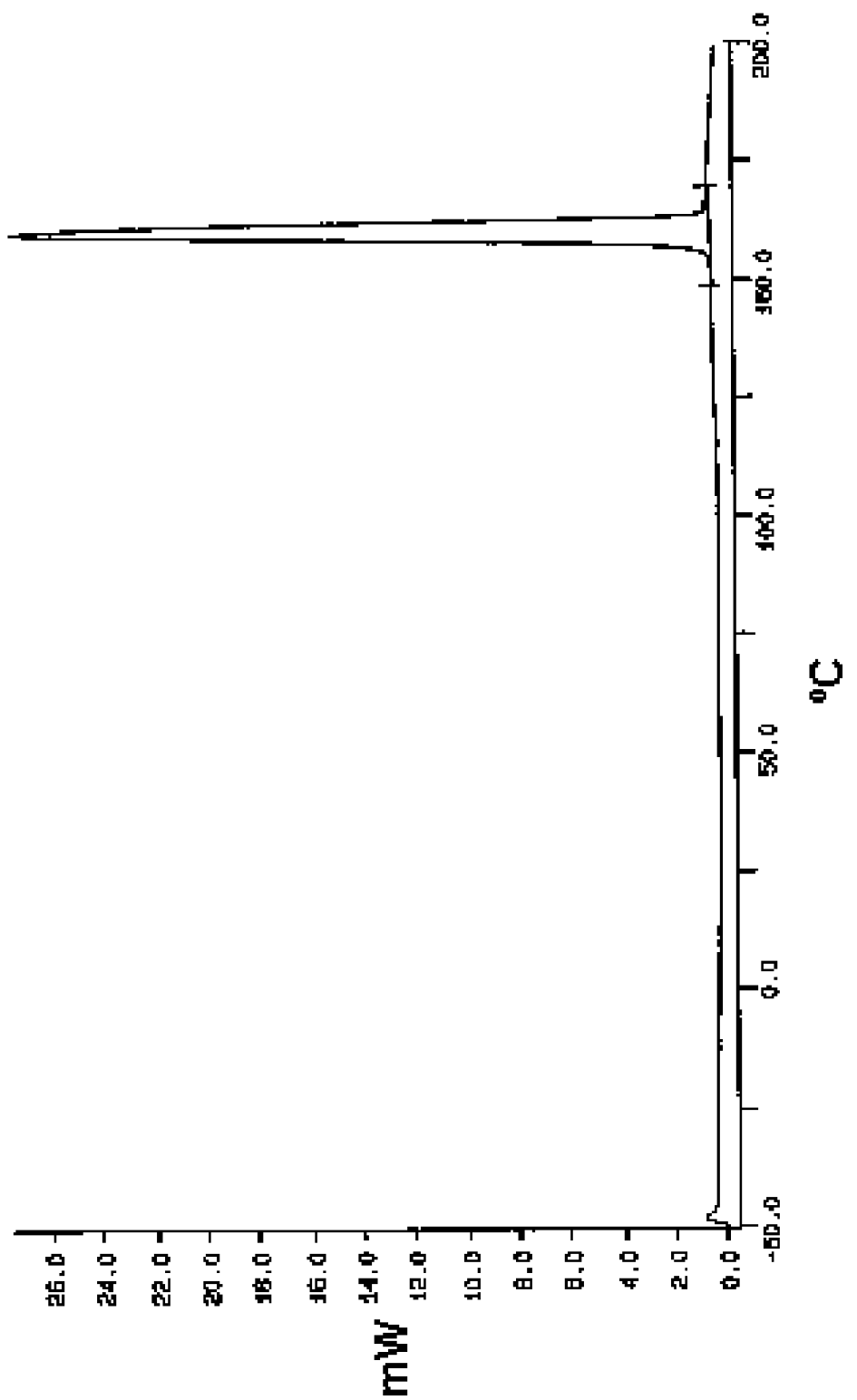
FIG. 3 is the Differential Scanning Calorimetry (DSC) curve of polymorph B.

Differential Scanning Calorimetry: The DSC measurement showed a sharp melting peak at approximately 158° C. with a melting enthalpy $\Delta_{fus}H$=104 J/g. The DSC curve is shown in FIG. 3.

Single crystal structure: The compound crystallized in the centro-symmetric space group P-1. The structure showed two molecules in the asymmetric unit which were not related by space group symmetry. These two molecules could be superimposed almost perfectly by rotation around the a axis, but the unit cell could not be transformed in order to gain higher lattice symmetry.

The structure could be interpreted as being based on dimers of the compound. The driving force for the formation of these dimers was most likely π-π interaction between the phenyl ring and the thiophene ring on the one hand and the N-heterocycles on the other hand. The two different types of molecules in the unit cell formed two different types of dimers with slightly different short distances between the condensed N-heterocycles (3.348 Å and 3.308 Å for the shortest distance, respectively). The dimers were arranged in layers with a fishbone structure. Bands of the two types of dimers always alternated in the fishbone structure, as well as they alternated from one layer to the next. The crystal data are reported in Table 1.

TABLE 1

| Crystal data for polymorph B | |
|---|---|
| Molecular formula | C$_{20}$H$_{15}$FN$_4$O$_2$S |
| Molecular weight | 394.43 g/mol |
| Molecules per unit cell Z | 4 |
| Calculated density | 1.478 g/cm$^3$ |
| Number of electrons per unit cell F(000) | 816 |
| Size of crystal | 0.14 × 0.18 × 0.24 mm$^3$ |
| Absorption coefficient | 0.218 mm$^{-1}$ |
| Min./max. transmission | 0.96/0.97 |
| Temperature | 173° K |
| Radiation (wavelength) | Mo Kα (α = 0.71073 Å) |
| Crystal system | triclinic |
| Space group | P-1 |
| a | 8.9236(2) Å |
| b | 14.0292(3) Å |
| c | 15.6218(3) Å |
| α | 65.3449(14)° |
| β | 87.0440(14)° |
| γ | 86.0799(14)° |
| Volume of the unit cell | 1772.69(7) Å$^3$ |
| Min./max. θ | 1.435°/27.883° |
| Number of collected reflections | 16548 |
| Number of independent reflections | 8448 (merging r = 0.034) |
| Number of observed reflections (I > 2.00σ(I)) | 5430 |
| Number of refined parameters | 506 |
| r (observed data) | 0.0455 |
| rW (all data) | 0.0734 |
| goodness of fit | 0.9980 |
| residual electron density | −0.37/0.39 e Å$^{-3}$ |

X-Ray diffractogram, FT-Raman spectrum and DSC curve are identical with disclosed in the referred European patent application entitled "Polymorph B of N-{2-Fluoro-5-[3-(thiophene-2-carbonyl)-pyrazolo[1,5-a]pyrimidin-7-yl]-phenyl}-N-methyl-acetamide" when compared by superposition. Moreover, crystal data are consistent with the reported in said application.

The invention claimed is:

1. A process for the industrial manufacture of polymorph B of N-{2-Fluoro-5-[3-(thiophene-2-carbonyl)-pyrazolo[1,5-a]pyrimidin-7-yl]-phenyl}-N-methyl-acetamide comprising the following steps:
   (i) reacting (5-amino-1H-pyrazol-4-yl)-thiophen-2-yl-methanone with N-[5-(3-dimethylamino-acryloyl)-2-fluoro-phenyl]-N-methyl-acetamide in a solvent selected from the group consisting of acetic acid, propionic acid, and formic acid at a temperature ranging from 50° C. to the boiling point of the mixture
   (ii) adding a ($C_1$-$C_4$)-alcohol; at a temperature comprised between 40° C. and 80° C.;
   (iii) aging for at least 30 min. at a temperature comprised between 30° C. and 55° C. to initiate the crystallization; and
   (iv) recovering the crystallized product.

2. The process according to claim 1, wherein the temperature in step (i) is comprised between 115° C. and 125° C.

3. The process according to any of the claims 1-2, wherein the alcohol in step (ii) is 2-propanol and it is added at a temperature comprised between 60° C. and 70° C.

4. The process according to claim 1, wherein the aging in step (iii) is carried out at a temperature comprised between 40° C. and 45° C.

5. The process according to claim 4, wherein the aging in step (iii) takes at least 1 hour.

6. The process according to claim 1, wherein the crystallized product is recovered in step (iv) by cooling the mixture at a temperature comprised between 0 and 10° C., followed by filtering the obtained product.

7. The process according to claim 6, wherein the mixture is maintained at a temperature comprised between 0-5° C. during at least 1 hour before the filtration.

8. The process according to claim 6, wherein the filtered product is dried at a temperature comprised between 45-55° C.

* * * * *